(12) United States Patent
Suehira (10) Patent No.: US 10,849,537 B2
(45) Date of Patent: Dec. 1, 2020

(54) PROCESSING APPARATUS AND PROCESSING METHOD

(71) Applicant: CANON KABUSHIKI KAISHA, Tokyo (JP)

(72) Inventor: Nobuhito Suehira, Tokyo (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 406 days.

(21) Appl. No.: 15/841,820

(22) Filed: Dec. 14, 2017

(65) Prior Publication Data

US 2018/0177442 A1 Jun. 28, 2018

(30) Foreign Application Priority Data

Dec. 22, 2016 (JP) .................. 2016-249008

(51) Int. Cl.
*A61B 5/1455* (2006.01)
*A61B 5/0205* (2006.01)
(Continued)

(52) U.S. Cl.
CPC ........ *A61B 5/14552* (2013.01); *A61B 5/0095* (2013.01); *A61B 5/0205* (2013.01); *A61B 5/14551* (2013.01); *A61B 5/4312* (2013.01); *A61B 5/708* (2013.01); *G06T 7/0012* (2013.01); *G06T 11/008* (2013.01); *A61B 5/024* (2013.01); *A61B 8/0825* (2013.01); *A61B 8/488* (2013.01); *A61B 2576/02* (2013.01); *G06T 2207/10048* (2013.01); *G06T 2207/10072* (2013.01); *G06T 2207/10132* (2013.01); *G06T 2207/30101* (2013.01)

(58) Field of Classification Search
CPC ... A61B 5/14552; A61B 5/708; A61B 5/4312; A61B 5/14551; A61B 5/0205; A61B 5/0095; A61B 2576/02; A61B 8/0825; A61B 5/024; A61B 8/488; G06T 11/008; G06T 7/0012; G06T 2207/10132; G06T 2207/30101; G06T 2207/10072; G06T 2207/10048
See application file for complete search history.

(56) References Cited

U.S. PATENT DOCUMENTS 3,998,550 A * 12/1976 Konishi ............. A61B 5/14551
356/39
2010/0007894 A1 1/2010 Suehira
(Continued)

FOREIGN PATENT DOCUMENTS

JP 2014-094225 5/2014

*Primary Examiner* — Eric F Winakur
*Assistant Examiner* — Abid A Mustansir
(74) *Attorney, Agent, or Firm* — Venable LLP (57) ABSTRACT

A processing apparatus having a processor acquiring image data indicating oxygen saturation distribution inside an object by using signals derived from acoustic waves generated from a plurality of wavelengths of light. The processor acquires an oxygen saturation at a first position of a blood vessel of the object, generated by image reconstruction using signals, acquires a first correction amount to correct the oxygen saturation at the first position of the blood vessel, and acquires a second correction amount to correct the oxygen saturation in a second position of the object other than the first position, based on the first correction amount.

15 Claims, 5 Drawing Sheets

(51) Int. Cl.
*A61B 5/00* (2006.01)
*G06T 11/00* (2006.01)
*G06T 7/00* (2017.01)
*A61B 8/08* (2006.01)
*A61B 5/024* (2006.01)

(56) References Cited

U.S. PATENT DOCUMENTS

| | | | |
|---|---|---|---|
| 2013/0197367 A1* | 8/2013 | Smok | A61B 8/085 600/454 |
| 2014/0336482 A1* | 11/2014 | Kasamatsu | A61B 5/0095 600/322 |
| 2015/0201843 A1* | 7/2015 | Koh | A61B 5/0095 600/407 |
| 2015/0238090 A1 | 8/2015 | Suita et al. | |
| 2015/0359519 A1 | 12/2015 | Suehira | |
| 2017/0065180 A1 | 3/2017 | Miyasato et al. | |
| 2017/0065181 A1 | 3/2017 | Masaki et al. | |
| 2017/0065252 A1 | 3/2017 | Suehira et al. | |
| 2017/0119253 A1 | 5/2017 | Suehira et al. | |
| 2017/0265749 A1 | 9/2017 | Suehira | |

\* cited by examiner

PROCESSING APPARATUS AND PROCESSING METHOD

BACKGROUND OF THE INVENTION

Field of the Invention

The present invention relates to a processing apparatus and a processing method.

Description of the Related Art

Recently photoacoustic tomography has been proposed as an optical imaging technique. The principle thereof is as follows. First a light, such as a pulsed laser light, is irradiated to an object so that the light is propagated and diffused inside the object. Then an absorber in the object, which absorbed the light energy, thermally expands and generates a photoacoustic wave. This photoacoustic wave is detected by an acoustic probe, and the detected signal is reconstructed, whereby a photoacoustic image is acquired.

Japanese Patent Application Laid-open No. 2014-094225 discloses a photoacoustic apparatus using near-infrared light. The near-infrared light is easily absorbed by blood vessels, hence the photoacoustic apparatus can acquire information on the distribution of the blood vessels. Further, by using light of a plurality of wavelengths, information on oxygen saturation of the blood vessels can be acquired.

Patent Literature 1: Japanese Patent Application Laid-open No. 2014-094225

SUMMARY OF THE INVENTION

By using the photoacoustic apparatus like this, information on the optical characteristics of the object, such as distribution of the blood vessels and information on oxygen saturations, can be acquired. According to the photoacoustic apparatus of Japanese Patent Application Laid-open No. 2014-094225, the oxygen saturations can be accurately calculated if the optical coefficient in the background are known.

Here it is assumed that normally the oxygen saturations in blood vessels which branch from a blood vessel are similar. However in some cases, the actual oxygen saturation values of the blood vessels calculated by the photoacoustic apparatus may vary depending on the location, even if these blood vessels branch from a same blood vessel. Further, the oxygen saturation values of arteries are normally constant in a 95% to 99% range, but in some cases, the oxygen saturation values actually calculated by the photoacoustic apparatus may exceed this range. In this way, the values calculated by the photoacoustic apparatus may not always reflect the actually oxygen saturation values, therefore an improvement in calculation accuracy is demanded.

With the foregoing in view, it is an object of the present invention to improve the accuracy of the oxygen saturation values calculated by the photoacoustic apparatus.

The present invention provides a processing apparatus comprising a processing unit configured to acquire image data indicating oxygen saturation distribution inside an object by using signals derived from acoustic waves which are generated by beams of light having a plurality of wavelengths irradiated to the object, wherein
the processing unit is configured to:
acquire information on an oxygen saturation at a first position of a blood vessel of the object, generated by image reconstruction using signals,
acquire a first correction amount to correct the information on the oxygen saturation at the first position of the blood vessel, and
acquire a second correction amount to correct information on the oxygen saturation in a second position of the object other than the first position, based on the first correction amount.

The present invention also provides a processing method for acquiring image data indicating information distribution on oxygen saturations inside the object by using signals derived from acoustic waves which are generated by beams of light having a plurality of wavelengths irradiated to an object, the method comprising:
acquiring an oxygen saturation at a first position of a blood vessel of the object, generated by image reconstruction using the signals;
acquiring a first correction amount to correct information on the oxygen saturation at the first position of the blood vessel; and
acquiring a second correction amount to correct information on an oxygen saturation in a second position of the object other than the first position, based on the first correction amount.

According to the present invention, the accuracy of the oxygen saturation values calculated by the photoacoustic apparatus can be improved.

Further features of the present invention will become apparent from the following description of exemplary embodiments with reference to the attached drawings.

DESCRIPTION OF THE EMBODIMENTS

Embodiments of the present invention will be described with reference to the drawings. The dimensions, materials, shapes and relative positions of the components described below should be changed appropriately depending on the configuration and various conditions of the apparatus to which the invention is applied. Therefore the scope of the present invention is not limited to the following description.

The present invention relates to a technique to detect an acoustic wave which propagates from an object, and generate and acquire characteristic information inside the object. This means that the present invention may be understood as: an object information acquiring apparatus or a control method thereof; an acoustic wave receiving apparatus or a control method thereof; an object information acquiring method; or a signal processing method. The present invention may also be understood as an image processing apparatus or an image processing method. Further, the present invention may be understood as a program which causes an information processing apparatus equipped with such hardware resources as a CPU and memory to execute these methods, or a computer-readable non-transitory storage medium storing this program.

The object information acquiring apparatus of the present invention includes a photoacoustic imaging apparatus which is configured such that when light (electromagnetic wave) is irradiated to an object, an acoustic wave generated inside the object by the photoacoustic effect is received, thereby the characteristic information of the object is acquired. In this case, the characteristic information is information on the characteristic value corresponding to each of a plurality of positions inside the object, and this characteristic value is generated using a receive signal which derived from the received photoacoustic wave.

The characteristic information acquired by the photoacoustic measurement refers to values reflecting the absorption amount and the absorptivity of the light energy. For example, the characteristic information includes a generation source of an acoustic wave which was generated by irradiating light having a single wavelength, an initial sound pressure inside the object, and a light energy absorption density and absorption coefficient which are derived from the initial sound pressure. Further, the concentration of a substance constituting a tissue can be acquired from the characteristic information acquired by beams of light having a plurality of mutually different wavelengths. If an oxyhemoglobin concentration and a deoxyhemoglobin concentration are determined as the substance concentration, an oxygen saturation distribution can be calculated. For the substance concentration, a glucose concentration, collagen concentration, melanin concentration, volume fraction of fat or water and the like may be determined.

Based on the characteristic information at each position inside the object, a two-dimensional or three-dimensional characteristic information distribution is acquired. The distribution data can be generated as image data. The characteristic information may be determined as distribution information at each position inside the object, instead of as numeric data. In other words, such distribution information as initial sound pressure distribution, energy absorption density distribution, absorption coefficient distribution, and oxygen saturation distribution may be determined.

The acoustic wave referred to in the present invention is typically an ultrasound wave, and includes an elastic wave called a "sound wave" and an "acoustic wave". An electric signal which was converted from an acoustic wave by a transducer, an acoustic converting element or the like is also called an "acoustic signal". The ultrasound wave or acoustic wave that is referred to in this description is not intended to limit the wavelength of the elastic wave. An acoustic wave generated by the photoacoustic effect is called a "photoacoustic wave" or a "light-induced ultrasound wave". An electric signal which is derived from a photoacoustic wave is also called a "photoacoustic signal".

In the following embodiment, a photoacoustic apparatus, which acquires distribution of light absorbers in an object by irradiating a pulsed light to the object and receiving and analyzing an acoustic wave from the object generated by the photoacoustic effect, will be described. This photoacoustic apparatus is suitable for the diagnosis of vascular diseases and malignant tumors of humans and animals, or for the follow-up observation of chemotherapy. Examples of the object are a part of a living body (e.g. a breast and hand of a patient), a non-human animal (e.g. mouse), an inanimate object and a phantom.

Example 1

Figure 1A:
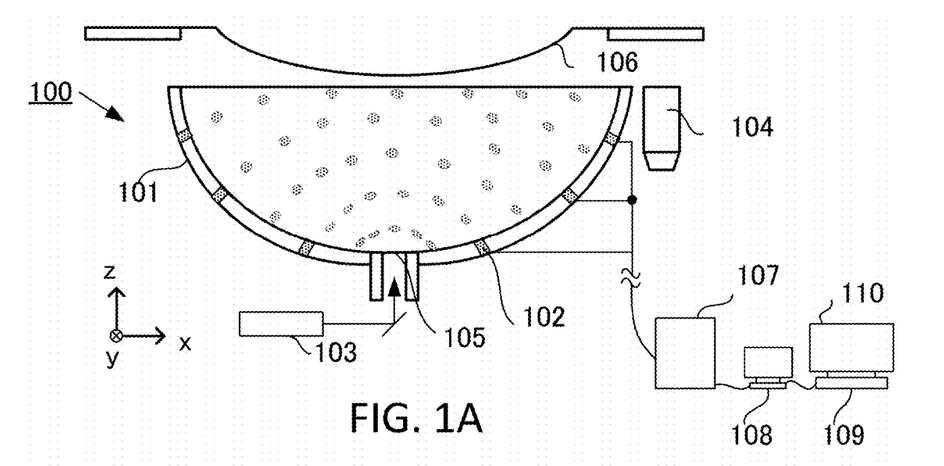
FIG. 1A and FIG. 1B are diagrams depicting the configuration of a photoacoustic apparatus of the present invention.
Figure 1B:
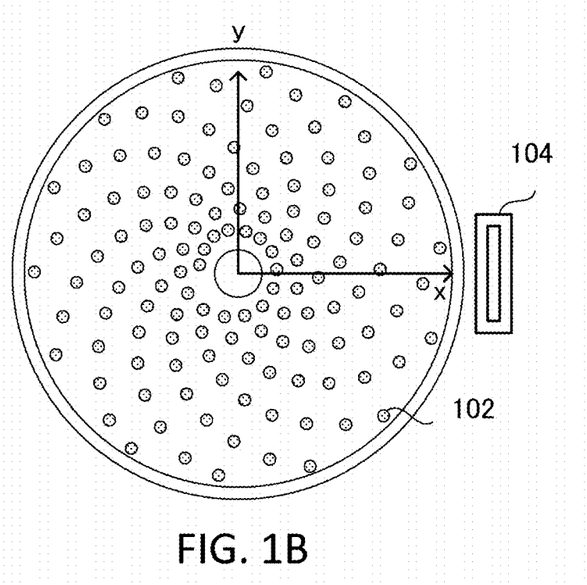

A photoacoustic apparatus according to this example is illustrated in FIG. 1A and FIG. 1B. FIG. 1A is a schematic diagram depicting a structure of the photoacoustic apparatus, where a cross-sectioned view of a probe unit 100 and a block diagram of an apparatus control unit are shown. FIG. 1B is a top view of the probe unit 100.

General Configuration

The probe unit 100 is constituted by 512 acoustic probes 102 disposed in a spiral along the inner surface of a support 101, which has a hemispheric container shape. On the bottom of the support 101, a space 105 is created, for allowing a measurement light, which is irradiated from a light irradiating unit 103 for generating a photoacoustic wave, to pass through. An object is disposed in a holding member 106, and the measurement light is irradiated from a negative direction on the z axis. It is preferable that an acoustic matching material, such as water, oil or gel, fills inside of the support 101 and the holding member 106 in order to improve the transmission efficiency of the photoacoustic wave. The relative positional relationship between the support 101 and the object can be changed by a scanning mechanism (not illustrated), such as an XY stage. By the scanning mechanism scanning the support 101, a wide range of the object can be measured.

The photoacoustic wave, which is propagated from the object and received by an acoustic probe 102, is converted into an electric signal, and outputted to a data acquiring unit 107. The data acquiring unit 107 performs amplification and AD conversion on the electric signal, and a data processing unit 109 reconstructs the electric signal, whereby a three-dimensional photoacoustic image, reflecting the optical characteristic value distribution inside the object, is acquired.

Separate from the acoustic probe 102, the photoacoustic apparatus of this example includes a linear type ultrasound probe 104, which is used for measuring the shape of the object. The linear type ultrasound probe 104 is configured such that scanning together with the support 101 is possible.

An apparatus control unit 108 sends commands for controlling the entire apparatus, such as light irradiation of the light irradiating unit 103, reception control of the data acquiring unit 107, movement of the XY stage, and transmission/reception of the ultrasound probe 104. The apparatus control unit 108 includes a user interface, so as to execute a change of measurement parameters, start/end of the measurement, selection of image processing method, saving of patient information and images, analysis of data and the like, based on an instruction from the operator. Furthermore, detailed data processing is executed by the data processing unit 109, and an analysis screen and the like are displayed on a display device 110.

Light Irradiating Unit

The light irradiating unit 103 includes a light source for a measurement light which excites a photoacoustic wave, and a light transmitting unit that transmits the measurement light to the object. For the light source, a laser light source is preferable in order to acquire high power. However a light emitting diode, a flash lamp or the like may be used. In the case of using laser, various lasers, such as a solid-state laser, a gas laser, a dye laser and a semiconductor laser, can be used. To effectively generate a photoacoustic wave, the light must be irradiated for a sufficiently short time in accordance with the thermal characteristic of the object. If the object is a living body, a pulsed light, of which pulse width is about 10 ns to 50 ns, is preferable. The wavelength of the pulsed light is preferably a wavelength with which the light can propagate into the object. In concrete terms, such a wavelength is at least 700 nm and not more than 1100 nm in the case of a living body.

In this example, a titanium sapphire laser, which is a solid-state laser, is used, and the wavelengths are 760 nm and 800 nm. By using beams of light with a plurality of wavelengths, information on oxygen saturation can be calculated based on the difference of absorption coefficients between the wavelengths. The timing, waveform, intensity and the like of the light irradiation are controlled by the apparatus control unit 108. The laser can alternately irradiate two beams of light in 10 Hz having different wavelengths. The apparatus control unit 108 appropriately acquires the received data, with interlocking the timings of the scanning of the probe unit 100, the light irradiation, and the acoustic wave reception, and saves the received data in a memory (not illustrated).

For the optical system, bundle fiber, a mirror, a prism, a lens and the like are preferable. Besides these components, any other optical components may be used as long as light can be irradiated to the object in a desired shape and at a desired intensity.

Acoustic Probe for Photoacoustic Wave

The acoustic probe 102 is an element that receives a photoacoustic wave. Typically the acoustic probe 102 is a piezoelectric ceramic (PZT) or a capacitive micro-machined probe (CMUT). CMUT is used in this example. The acoustic probe 102 is a single element having a φ3 mm opening, a 0.5 MHz to 4 MHz band, and a 0.5 mm resolution. Since the low frequency band is included, a good image can be acquired even from a blood vessel of which thickness is about 3 mm. In other words, a state in which a blood vessel appears to be transparent inside, as if a cross-section thereof is ring-shaped, is not generated very much. The sample frequency is 40 MHz, and 2048 sampling is performed. The data to be acquired is signed 12-bit data.

Data Acquiring Unit

The signal converted into an electric signal by the acoustic probe 102 is transmitted to the data acquiring unit 107, is amplified by the amplifier, is converted into a digital signal by an A/D converter, and is saved as data in a storage unit (not illustrated) such as a flash memory and an HDD. In this case, the storage unit may be a storage unit included in the data acquiring unit 107 or the apparatus control unit 108, or may be an external storage device. In other words, the present invention may be understood as an invention on a photoacoustic apparatus, or an invention on an information processing apparatus or an image processing method for processing data which the photoacoustic apparatus acquired and saved in the storage unit. Typically the data acquiring unit 107 is constituted by an amplifier, an A/D converter, a FPGA chip and the like.

Apparatus Control Unit

The apparatus control unit 108 is an information processing apparatus that includes a processor (e.g. CPU, GPU), a memory (e.g. ROM, RAM), a communication device, a user interface, and other resources, and operates according to each step of the program developed in the memory. Each function of the apparatus control unit 108 may be implemented by a combination of a plurality of apparatuses. The user interface is, for example, an input apparatus into which the user inputs information, such as a mouse, keyboard and touch panel, or an input apparatus using voice or image.

Linear Type Ultrasound Probe

The linear type ultrasound probe 104 transmits/receives an ultrasound wave to/from an object, and acquires a form image or a doppler image. In this example, a probe, in which 256 PZT elements are disposed, is used as the linear type ultrasound probe. The element has a 5 MHz to 10 MHz band. The sampling frequency is 40 MHz, and 2048 sampling is performed. Instead of disposing the linear type ultrasound probe 104, the probe unit 100 may be used to transmit the ultrasound wave and to receive the echo wave.

Support

For the support 101, it is preferable to use a member having a sufficient durability and strength to sustain the weight of the acoustic matching material, and to endure the movement of the scanning mechanism. Typically metal or resin is used. In this example, a hemispheric-shaped support 101 is used. This is because a high sensitivity region, where the respective high sensitivity directions (directional axes) of the plurality of acoustic probes 102 concentrate, is generated, whereby the accuracy of acquiring the characteristic information distribution of the object improves. As illustrated in FIG. 1B, the plurality of acoustic probes 102 are disposed in a three-dimensional spiral form in this example, but the manner of disposing the acoustic probes 102 is not limited to this. The shape of the support is not limited to a hemisphere, but may be linear, planer, bowl-shaped or the like.

Holding Member

For the holding member 106, a member having the strength to support the object and having characteristics to transmit light and the acoustic wave are used. A preferable material is polyethylene terephthalate, acryl or the like. A thin rubber, film or the like may be used. The shape of the holding member 106 is preferably similar to the shape of the object. For example, if the object is a breast, a cup type holding member 106 is used.

Data Processing Unit

The data processing unit 109 generates a photoacoustic image inside the object and an oxygen saturation image which is a functional image, by image reconstruction using photoacoustic signals saved in the storage unit. The data processing unit 109 also performs other required processing, such as image processing to calculate light quantity distribution and acquire optical coefficients of the background, and signal correction. The data processing unit 109 can be constructed by an information processing apparatus which includes a processor and memory. Each function of the data processing unit can be implemented by each module of a program which runs on the processor. The apparatus control unit 108 and the data processing unit 109 may be constructed by a common image processing apparatus. The data processing unit 109 corresponds to the processing unit of the present invention.

The photoacoustic image and the oxygen saturation image are displayed on the display device 110. A 30 inch display device with a contrast ratio of at least 1000:1 is preferred, since color display at high resolution is possible. Any display, such as a liquid crystal display, a plasma display and an organic EL display, can be used as the display device 110.

Image Reconstruction

Detailed image reconstruction is performed by the data processing unit 109. For the image reconstruction, a known reconstruction method, such as the universal back projection method and the delay-and-sum method, is used. In this example, the universal back projection method is used. The initial sound pressure distribution P (r), which is generated in the photoacoustic measurement, is given by Expression (1).

[Math. 1]

$$P(r) = \int_{\Omega_0} b(r_0, t = |r - r_0|) \frac{d\Omega_0}{\Omega_0} \quad (1)$$

The term b ($r_0$, t), which corresponds to the projection data, is given by Expression (2). Here pd ($r_0$) denotes a photoacoustic signal detected by the acoustic probe 102, $r_0$ denotes a position of each acoustic probe 102, t denotes time, and $n_0$ denotes a solid angle of the acoustic probe 102. The data acquired by the data acquiring unit 107 is processed based on Expression (1), whereby the initial sound pressure distribution P(r) can be acquired.

[Math. 2]

$$b(r_0, t) = 2p_d(r_0, t) - 2t \frac{\partial p_d(r_0, t)}{\partial t} \quad (2)$$

The absorption coefficient distribution is calculated from the initial sound pressure distribution P(r). The sound pressure P(r), which is generated when light is irradiated to an absorber, is given by Expression (3).

[Math. 3]

$$P(r) = \Gamma \cdot \mu_a(r) \cdot \Phi(r) \quad (3)$$

F denotes a Grüneisen coefficient, which is an elastic characteristic value, and is determined by dividing the product of the volume expansion coefficient (β) and a square of the sound velocity (c) by a specific heat (Cp). $\mu_a$ denotes an absorption coefficient of the absorber. φ(r) denotes a quantity of light which is irradiated to the absorber in a local region. By solving Expression (3) for the absorption coefficient, the absorption coefficient distribution $\mu_a(r)$ can be acquired. The optical coefficient of the background, which is sufficiently smaller than the absorption coefficient of the absorber, is not included in the absorption coefficient distribution.

In the case when light evenly attenuates in the depth direction, the light quantity distribution φ(r) can be given by Expression (4), for example, using a z variable.

[Math. 4]

$$\Phi = \Phi_0 \, EXP(-\mu_{\mathit{eff}} z) \quad (4)$$

Here $\phi_0$ denotes a light quantity of the incoming light on the surface. $\mu_{\mathit{eff}}$ denotes an averaged equivalent attenuation coefficient within the object, which reflects the scattering coefficient $\mu_{bs}$ and the absorption coefficient $\mu_{ba}$ of the background within the object, and can be given by Expression (5), for example.

[Math. 5]

$$\mu_{\mathit{eff}} = \sqrt{3\mu_{ba}\mu_{bs}} \quad (5)$$

The scattering coefficient and the absorption coefficient of the background within the object can be measured by a near-infrared spectroscopic apparatus, for example. However, in this case, numeric values are calculated based on the assumption that the object is a homogeneous medium, hence it is difficult to calculate these values accurately in a breast, which has various structures, such as skin, fat layers, mammary gland layers and blood vessels. In the present invention, a value corresponding to gender, age, weight and the like may be selected from an optical coefficient distribution in the background which was acquired in advance. It is sufficient if the image of the optical coefficient distribution allows distinguishing between arteries and veins, and this image is used for correction in later steps.

Now a method for determining a hemoglobin distribution from the absorption coefficient distribution will be described. The absorption coefficient $\mu_a(\lambda)$ of an absorber is determined by the respective absorption of oxyhemoglobin CHbO and deoxyhemoglobin CHbR per unit volume. If the absorption coefficient of the oxyhemoglobin and that of the deoxyhemoglobin at each wavelength $\lambda_1$ and $\lambda_2$ are EHbO ($\lambda_1$), EHbR($\lambda_1$), EHbO($\lambda_2$) and EHbR($\lambda_2$), the formulae in Expression (6) are established. The left side of the formulae indicates the absorption coefficient distribution acquired by Expression (3).

[Math. 6]

$$\mu_a(\lambda_1) = \epsilon_{HbO}(\lambda_1)C_{HbO} + \epsilon_{HbR}(\lambda_1)C_{HbR}$$

$$\mu_a(\lambda_2) = \epsilon_{HbO}(\lambda_2)C_{HbO} + \epsilon_{HbR}(\lambda_2)C_{HbR} \quad (6)$$

If Expression (6) is transformed for the oxyhemoglobin and the deoxyhemoglobin respectively, the formulae in Expression (7) are established.

[Math. 7]

$$C_{HbO} = \frac{\epsilon_{HbR}(\lambda_2)\mu_a(\lambda_1) - \epsilon_{HbR}(\lambda_1)\mu_a(\lambda_2)}{\epsilon_{HbO}(\lambda_1)\epsilon_{HbR}(\lambda_2) - \epsilon_{HbR}(\lambda_1)\epsilon_{HbO}(\lambda_2)}$$

$$C_{HbR} = \frac{\epsilon_{HbO}(\lambda_1)\mu_a(\lambda_2) - \epsilon_{HbO}(\lambda_2)\mu_a(\lambda_1)}{\epsilon_{HbO}(\lambda_1)\epsilon_{HbR}(\lambda_2) - \epsilon_{HbR}(\lambda_1)\epsilon_{HbO}(\lambda_2)} \quad (7)$$

The total hemoglobin (tHb), which is the total amount of the oxyhemoglobin and the deoxyhemoglobin, is given by Expression (8).

[Math. 8]

$$t_{Hb} = C_{HbO} + C_{HbR} \quad (8)$$

The oxygen saturation StO, which is the ratio of the oxyhemoglobin to the total hemoglobin, is given by Expression (9).

[Math. 9]

$$StO = \frac{C_{HbO}}{C_{HbR} + C_{HbO}} \quad (9)$$

Processing Flow

Figure 2:
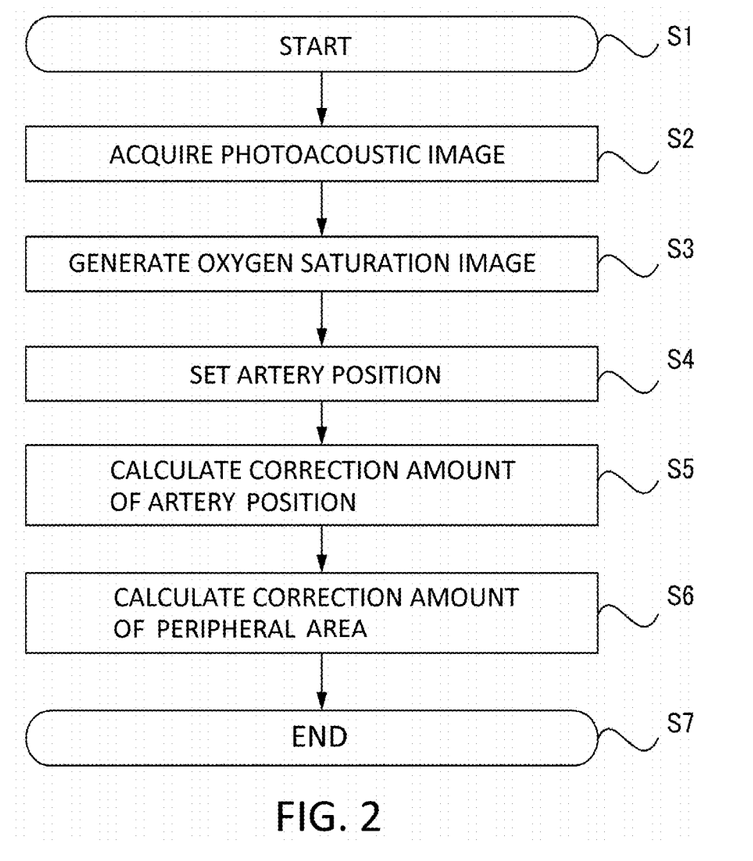
FIG. 2 is a flow chart depicting a processing of the present invention.

FIG. 2 is a flow chart of the processing of the present invention.

In step S1, a measurement is started. In this state, an object is inserted so as to contact the holding member 106. The holding member 106 and the object contact each other such that no air enters there between, and water, which is an acoustic matching material, is filled around the object. An ultrasound measurement may be performed using the ultrasound probe 104 before acquiring the photoacoustic image. By this ultrasound image, the coordinates of a lesion part of the object, for example, can be specified. The oxygen saturation may be measured by optical measurement using a pulse oximeter. In this case, an oxygen saturation of a finger is measured using a standard transmission type pulse oximeter. However, the present invention is not limited to this, and other regions may be measured using a reflection type pulse oximeter.

In step S2, the photoacoustic measurement is performed. First the operator instructs the measurement via the user interface of the apparatus control unit 108. Thereby the XY stage, which is a scanning mechanism, moves the support 101 to a desired position. Then the light irradiation unit 103 irradiates the pulsed light, and synchronizing with this irradiation, the acoustic probe 102 receives the photoacoustic wave. When the pulsed light is irradiated, two beams of light with wavelengths of 760 nm and 800 nm are alternately irradiated, while spirally moving the support 101. Finally each photoacoustic wave with a respective wavelength is acquired at the position 1024. The imaging can be selected out of an 80 mm, 120 mm and 160 mm diameter range. If the photoacoustic images are acquired using two different wavelengths, by alternately irradiating beams of light with different wavelengths, the influence of positional deviation of the images between the wavelengths, due to body movement or the like, can be decreased, compared with photoacoustic images acquired by measuring the object twice using light having each wavelength respectively. The electric signals, generated by being converted from the photoacoustic wave and then being digitized, are stored in the storage device.

In step S3, a functional image is generated from the photoacoustic image. The data processing unit 109 reads the receive data from the storage device, reconstructs the image, and acquires the initial sound pressure distribution for each wavelength. Then the data processing unit 109 acquires the absorption coefficient distribution for each wavelength using the initial sound pressure distribution and the light quantity distribution. Then the data processing unit 109 acquires the oxygen saturation image, which is a functional image. The functional image can be calculated using signals generated after removing the noise components from the initial sound pressure distribution or the like, via a filter. For the filter, a standard smoothing filter, Gaussian filter, median filter, bilateral filter or the like is used. This is for preventing the influence of local noise. For the oxygen saturation, it is preferable to display portions that are not less than the threshold selected from the absorption coefficient distribution. Thereby only the positions of the blood vessels can be displayed.

The light quantity distribution can be acquired by calculation using the optical coefficients of the background of the object and the form information of the object. In the case of this example, the form information can be calculated based on the ultrasound echo data acquired by the ultrasound probe 104. The boundary of the object may be extracted from the initial sound pressure distribution image acquired by reconstruction. Further, if the object is held inside the holding member 106, the shape of the holding member 106 may simply be regarded as the shape of the object.

In step S4, a position (first position) that was determined as an artery is set in the object. This will be described with reference to an analysis screen 300 in FIG. 3. The analysis screen 300 is displayed on the display device 110, and is constituted by, for instance, a functional image display portion 301, a pointer 305, assist lines 303 and 304 to indicate the x coordinate and the y coordinate of the center of the pointer, a histogram 302 of the pointer portion, and display areas 306 and 307 for the oxygen saturation. The histogram 302 indicates the appearance frequency for each numeric value range of the oxygen saturation value (%) in each of the 12×12 pixels included in the pointer.

Figure 3:
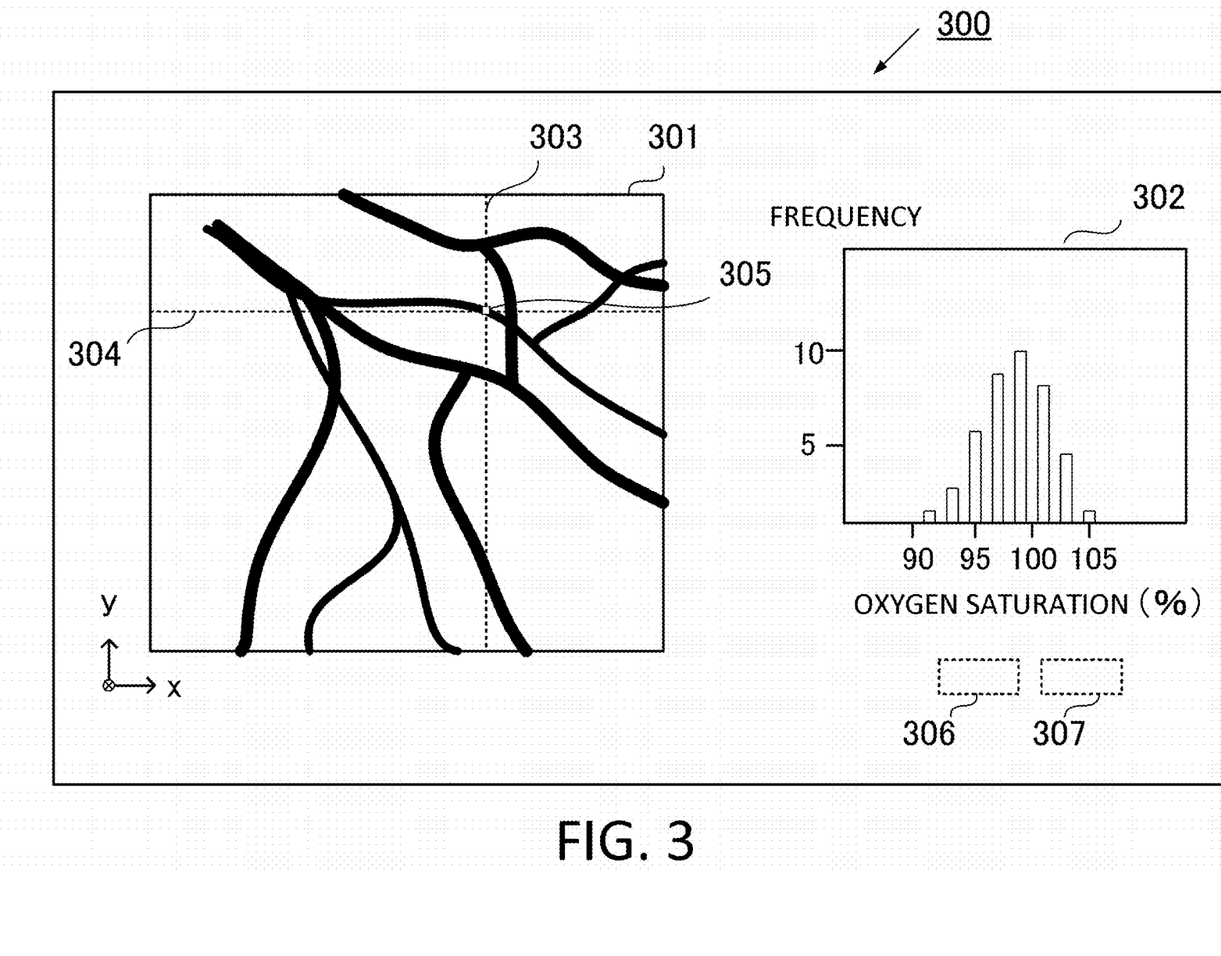
FIG. 3 is a diagram depicting an analysis screen provided by the present invention.

In the analysis screen 300, the operator can set a number of pages of the image in the depth direction that is used for the maximum value projection, a start position in the depth direction for the maximum value projection, the zoom in/out function of the image and the like, using the input apparatus. Here the maximum value projection refers to acquiring the maximum absorption coefficient value in the z direction at each point of the xy plane, acquiring the oxygen saturation value at the position which indicates the maximum absorption coefficient value, and arranging each acquired oxygen saturation values on the xy plane. Thereby the oxygen saturation at blood vessel positions, where the absorption coefficient is high, can be selectively displayed. This image is hereafter called the "oxygen saturation projection image".

Concerning the resolution of the image in this example, it is assumed that one pixel (or voxel) has a width of 0.0625 mm. The imaging region to be displayed is in a 50×50 mm range. The pointer portion is constituted by 12×12 pixels, and can be moved by the operator using the input apparatus. The average value and the variance value of the oxygen saturation value in the pointer portion can be displayed in the display areas 306 and 307 respectively.

Figure 4A:
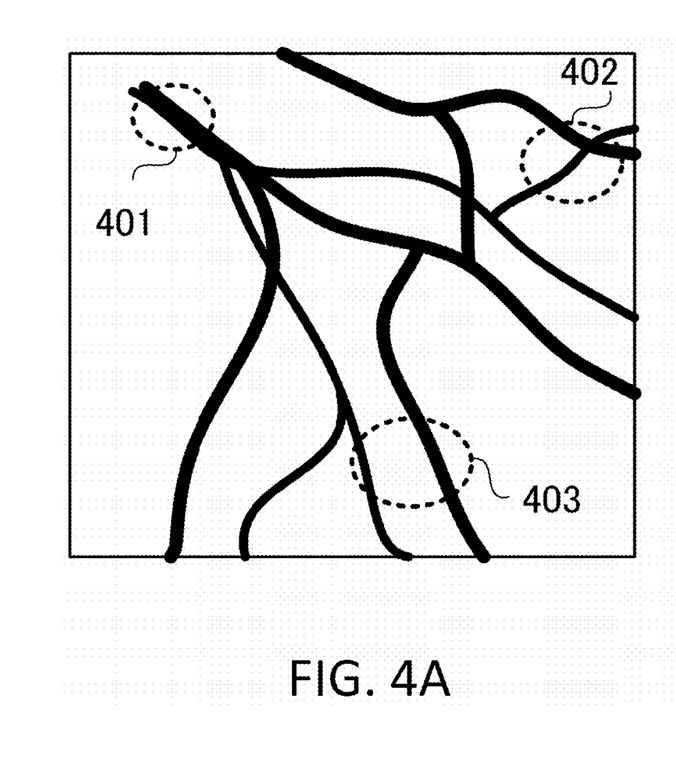
FIG. 4A and FIG. 4B are diagrams depicting the positions of blood vessels on the analysis screen.

FIG. 4A is an example of the oxygen saturation projection image, which is displayed in the functional image display portion 301 in FIG. 3. Thus far, in a predetermined region of the skin of the object, the maximum value of the absorption coefficient at each position in the depth direction is determined within a range of a predetermined depth (10 mm in this example) from the surface of the skin, then the oxygen saturation value is determined at the depth where the absorption coefficient value is the maximum. FIG. 4A is a schematic diagram in the coronal direction when the breast is viewed from the front.

Figure 4B:
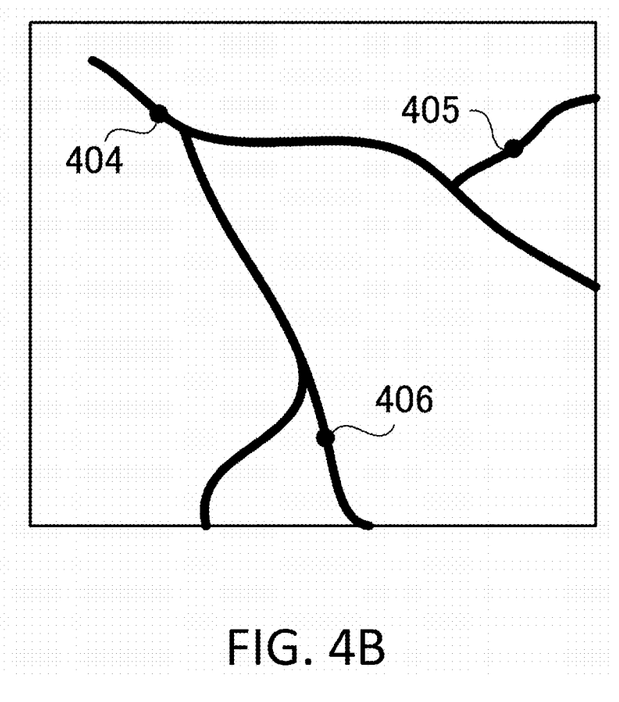

FIG. 4B is a diagram depicting a plurality of first positions (marks 404 to 406) selected in an artery. There is an internal mammary artery in the direction of the region 401 with respect to the center of FIG. 4A, and there is a nipple in the direction of the region 403. Here the oxygen saturation projection image is displayed as a monochrome image, but it is preferable to use a color map, where gradation in accordance with the oxygen saturation is displayed, from the 0% oxygen saturation as blue to the 100% oxygen saturation as red.

To specify an artery in the photoacoustic image, the following information (1) to (5) is used.

(1) An Artery and a Vein Form a Pair.

The blood that exits an artery moves through tissues in the body, and returns to a vein. When two blood vessels run close to each other (e.g. a distance not more than 10 mm), it is assumed that one is an artery and the other is a vein. If two blood vessels branch from one blood vessel, these branched blood vessels are of course the same type of blood vessels. In the case when the object is a breast, a portion where an artery and a vein accompany each other, running side by side, may be observed in a portion where the blood vessels branch directly from an internal mammary artery. This is a typical example of an artery and a vein which form a pair, and special attention is required since one of this pair is definitely an artery. In FIG. 4A, the region 401 is the accompanying portion. In the region 402 and region 403 as well, it is determined that an artery and a vein form a pair. This, however, does not always mean that blood flows between the artery and the vein.

(2) The Oxygen Saturation of an Artery is Higher than that of Vein.

The oxygen saturation value is about 95% to 99% in an artery, and about 60% to 80% in a vein. Whether a blood vessel is an artery or a vein can be estimated by the range of the numeric values of the blood vessels. In actual measurement, however, the calculated values may not come within these ranges, because of the influence of the shapes, the optical coefficient of the background, noise and the like. But even in such a case, the relative magnitude relationship of the oxygen saturations between an artery and a vein, which form a pair in a shallow position, is rarely reversed. This is because an error in the light quantity distribution increases as the position is deeper, as expressed in Expression (4). For example, if the oxygen saturation of one of a pair of the blood vessels is 105% and that of the other is about 90%, it is assumed that the blood vessel of which oxygen saturation value is relatively high is an artery. An error in the calculated value of the oxygen saturation value from the actual value is smaller as the location is closer to the surface of the object. Therefore it is better to compare blood vessels which form a pair, using the oxygen saturation value of a blood vessel closer to the surface, out of the pair of blood vessels, as a reference.

(3) An Artery is Normally Thinner than a Vein.

For example, if two blood vessels run close to each other (a distance of not more than 10 mm), the thinner blood vessel can be presumed to be an artery. However, the values of the oxygen saturation are used for this determination with priority.

(4) Continuous Portions are the Same Kind of Blood Vessel.

In some cases, even if there is a tubular absorber in the image, which is presumed to be a blood vessel, partially great levels of noise may make it difficult to discern whether this is an artery or a vein. In other cases, in a portion where the blood vessels form a pair and accompany each other, the calculated oxygen saturation values of these two blood vessels may be close (e.g. 95%). The cause of this is unknown, but may be due to the mix of signals because blood vessels of similar diameters (e.g. 1 mm) come close to each other. In yet other cases, the actual light quantity distribution may be different from the assumed physical model, or these close values may not be in error, because the oxygen in the artery is not consumed and the blood returns to the vein since the blood vessels are located close to each other. Even in such cases, an artery can be determined based on the fact that one continuous blood vessel is either an artery or a vein, and the type of blood vessel never changes in the middle of a blood vessel. In other words, even in the case when there is a portion in a tubular absorber where an artery or a vein cannot be determined, it can be determined that the entire tubular absorber is an artery only if another portion of this tubular absorber is detected as an artery. In the case of a breast, blood vessels branch from specific artery such as an inner mammary artery and an outer mammary artery, therefor if a part of the continuous vessel is determined to be an artery, the other portions can be determined to be an artery relatively easily.

(5) An Artery is Located Deeper than a Vein.

If a blood vessel tapers off from a deep position to a shallow position in an image, this blood vessel is inferred to be an artery. On the other hand, if a blood vessel runs along the surface without changing a 2 to 3 mm thickness, this blood vessel can be inferred to be a vein. To determine whether a blood vessel is located at a deep position, an axial image, in which the breast is projected to the plane on the head side, and a sagittal image in which the breast is projected to the plane in parallel with the head to toe direction (perpendicular to the direction of the axial image), may be used. However the values of the oxygen saturations are used for this determination with priority.

In the case when the apparatus includes a linear type ultrasound probe 104 and the ultrasound probe 104 can move to a desired position, as in the case of this example, an artery may be determined by observing pulses using a doppler method. It is difficult to detect a doppler signal from a thin blood vessel, but a doppler signal can be detected in some cases from an artery of which diameter is about 2 mm, located in a position near an internal mammary artery.

The first position in the blood vessel may be set by the operator using an input apparatus based on the above mentioned information, or may be set by the data processing unit, analyzing the image based on the above mentioned information. In the former case, the user interface is regarded as the input apparatus which receives input. As more first positions are inputted, more detailed corrections can be set. The thicker a blood vessel to be selected the better, such as at least 1 mm. This is because a thin blood vessel is more easily influenced by an error generated due to body motion or the like, and is more easily affected by noise. Therefore only blood vessels having at least a predetermined thickness may be displayed. The thickness can be determined based on a number of pixels in each of the x, y and z directions when pixels having approximately the same oxygen saturation are continuous.

Further, a position of an artery may be extracted by the image processing of the data processing unit. An artery is extracted by setting a start point of an artery in the oxygen saturation image, and sequentially connecting points of which the oxygen saturation is close to the previous point. For a portion where blood vessels cross each other or for a portion where blood vessels run accompanying each other, the operator may make an appropriate decision and correct the extraction of an artery. Template processing may be performed for the blood vessel image.

The position of the artery is inputted by disposing marks 404 to 406 on the image, as illustrated in FIG. 4B. A mark is disposed by displaying a point on the image, as illustrated in FIG. 3, and clicking using a mouse or the like. In this case, the operator sets an appropriate position while viewing a histogram and average value of the oxygen saturations. If pixels, which indicate 90% to 105% of the oxygen saturation values, concentrate in a narrow range of the histogram (e.g. bars indicating a high frequency, concentrated in a ±1% range in the oxygen saturations), it can be determined that the position of the pointer is an artery position. If the appearance frequency disperses, on the other hand, the position of the pointer cannot be determined as an artery position, because, for instance, many noise components may exist; a portion other than blood vessels are included; or an artery and a vein may exist close to each other. An alarm may be visually displayed when such a position is set.

It is preferable to select an artery from a normal segment. This is because the acquired oxygen saturation values of the artery could be roughly uniform if it is a normal segment. In a lesion segment, on the other hand, the oxygen saturation may drop due to a decrease in the partial oxygen pressure. To discern a lesion segment from a normal segment, a range which is suspected to be a tumor segment may be masked based on a three-dimensional ultrasound image acquired by the linear type ultrasound probe 104, or an image separately acquired by MRI or the like, so that marks to indicate an artery can be disposed only in the other segments (normal segments).

In step S5, the correction amount at the artery position is calculated. It is normally assumed that the oxygen saturation of an artery is unchanged within a body. Therefore a value measured by optical measurement using an oxygen saturation measuring instrument, such as a pulse oximeter, can be regarded as an oxygen saturation value of the artery. If an oxygen saturation at an artery position is 102% and a measurement value by the pulse oximeter is 98%, then the correction amount is −4%. This correction amount is a correction amount at a first position of the artery, and corresponds to the first correction amount of the present invention. The correctable range may be limited so that the correction amount is not influenced by local noise.

Figure 5A:
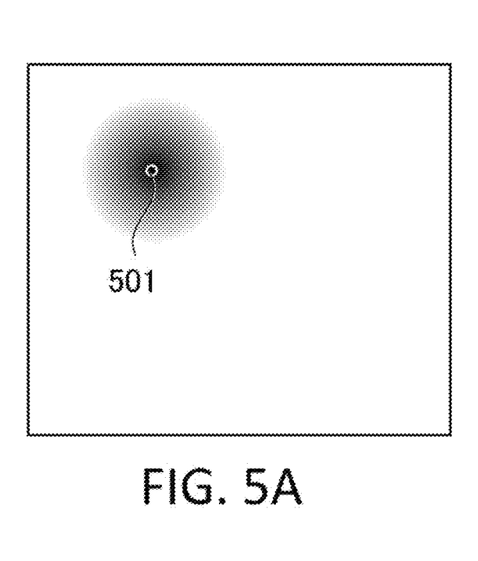
FIG. 5A to FIG. 5C are diagrams depicting a method of determining the correction amount for a peripheral area according to the present invention.

In step S6, the correction amount in a peripheral area of the artery position is calculated. This correction amount is for correcting the oxygen saturation in a portion other than a specific portion, and corresponds to the second correction amount of the present invention. The method of correcting the peripheral area will be described with reference to FIG. 5A to FIG. 5C. In this step, the oxygen saturations of arteries and veins included in the peripheral area are corrected. FIG. 5A is a case when there is only one artery position. In this example, correction is made at mark 404 in FIG. 4B, which is located close to the internal mammary artery. An artery located close to the internal mammary artery is thick, hence the oxygen saturation value thereof is presumed to be more reliable. This is because the calculated value in step S3 is close to the value measured by the pulse oximeter, and noise can be reduced by increasing the number of sampling points of the oxygen saturations, which are calculated by the photoacoustic apparatus.

The coordinates of the mark 404 in FIG. 4B are coordinates 501 (x1, y1), and the correction amount thereof is d1(%). Here the correction is made such that the correction amount in the peripheral area around the coordinates (x1, y1) is minimized. For example, a correction target is set to a region within a 30 mm distance from a first position of an artery. Then the influence of correction is limited to the peripheral area of the artery position, thereby the local correction does not influence the entire object. In the case when the numeric values of the oxygen saturations uniformly shift in general, the correction may be reflected in the entire object. If an artery is extracted, as illustrated in FIG. 4B, the correction may be performed such that a correction amount in each position of the artery is calculated first, and the peripheral area of the artery is corrected using a correction amount of the artery at the closest distance.

Figure 5B:
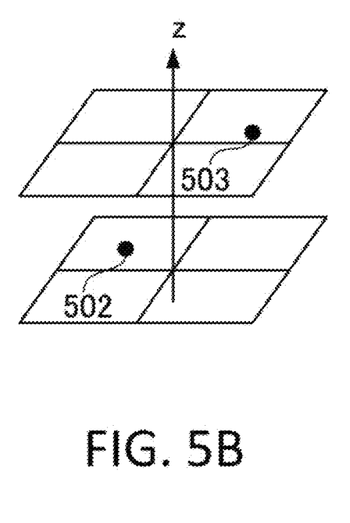

FIG. 5B is a case when there are two artery positions which are specified. The coordinates corresponding to the marks 404 and 405 in FIG. 4B are coordinates 502 (x2, y2, z2) and 503 (x3, y3, z3) respectively, and the correction amounts thereof are d2 and d3(%) respectively. The z position indicates the depth of the xy coordinates at which the oxygen saturation is the maximum. The coordinates 502, which are close to the internal mammary artery, is deeper (more distant from the surface), and the coordinates 503, which branch from the artery, is shallower (closer to the surface). The correction amount of the peripheral area can be determined by interpolation or extrapolation based on the correction amounts of the positions at z1 and z2. The method of interpolation is not limited, and may be linear interpolation or interpolation using exponential functions. In this case, the same correction amount is used if the depth is the same.

Figure 5C:
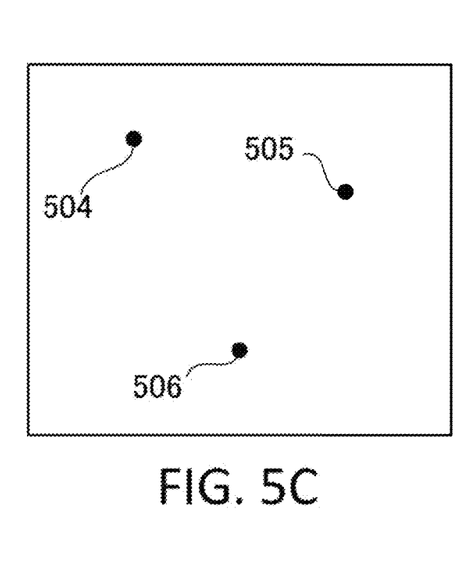

FIG. 5C is a case when there are three artery positions which are specified. The coordinates corresponding to the marks 404, 405 and 406 in FIG. 4B are the coordinates 504 (x1, y1), 505 (x2, y2) and 506 (x3, y3) respectively, and the correction amounts thereof are d1, d2 and d3(%) respectively. In this case, the correction amount of the peripheral area on the xy plane can be determined by a plane equation. As a number of marks in FIG. 4B increase, the correction amount of a peripheral area can be determined in more detail.

If the values of the oxygen saturations are calculated to be slightly higher or lower than the actual values in the artery or vein, due to the characteristics of the apparatus, then only one, the artery or the vein in which values are calculated to be higher or lower, may be further corrected.

The above mentioned processing operations may be appropriately combined. In this way, the oxygen saturations are corrected, and the oxygen saturation image can be acquired.

Then processing ends in step S7.

As described above, in the photoacoustic apparatus according to the present invention, the calculated values of the oxygen saturations can be corrected to within an appropriate range, based on the oxygen saturation of an artery, which should be roughly constant regardless the location. As a result, the accuracy of the display image, which indicates the oxygen saturation distribution, can be improved, and a good diagnosis can be implemented.

Other Embodiments

Embodiment(s) of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiment(s) and/or that includes one or more circuits (e.g., application specific integrated circuit (ASIC)) for performing the functions of one or more of the above-described embodiment(s), and by a method performed by the computer of the system or apparatus by, for example, reading out and executing the computer executable instructions from the storage medium to perform the functions of one or more of the above-described embodiment(s) and/or controlling the one or more circuits to perform the functions of one or more of the above-described embodiment(s). The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™) a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2016-249008, filed on Dec. 22, 2016, which is hereby incorporated by reference herein in its entirety.

What is claimed is:

1. A processing apparatus comprising:
a processing unit configured to acquire image data indicating oxygen saturation distribution inside an object by using signals derived from acoustic waves which are generated by beams of light having a plurality of wavelengths irradiated to the object, wherein the processing unit is configured to:
acquire information on an oxygen saturation at a first position of a blood vessel of the object, generated by image reconstruction using the signals,
acquire a first correction amount to correct the information on the oxygen saturation at the first position of the blood vessel,
acquire a second correction amount to correct information on the oxygen saturation in a second position of the object other than the first position, based on the first correction amount, and
correct information on the oxygen saturation in a peripheral area of the first position of the blood vessel by using the second correction amount; and
a storage unit configured to store the information on an oxygen saturation at a first position, the first correction amount, and the second correction amount so as to be readable by the processing unit.

2. The processing apparatus according to claim 1, wherein the blood vessel is an artery.

3. The processing apparatus according to claim 1, wherein the processing unit is configured to correct information on the oxygen saturation in a region located at a predetermined distance from the first position of the blood vessel by using the second correction amount.

4. The processing apparatus according to claim 1, wherein the processing unit is configured to set the first position, based on the input performed by an operator using an input apparatus.

5. The processing apparatus according to claim 4, wherein the input apparatus is configured to receive input by the operator, based on a projection image of information on the oxygen saturations from the surface to a predetermined depth of the object.

6. The processing apparatus according to claim 1, wherein the processing unit is configured to set the first position by analyzing an image acquired by the image reconstruction.

7. The processing apparatus according to claim 1, wherein the processing unit is configured to acquire information on the oxygen saturations at a plurality of first positions in the blood vessel of the object.

8. The processing apparatus according to claim 1, wherein the processing unit is configured to acquire the first correction amount, based on the information on the oxygen saturation generated by the image reconstruction at the first position, and the oxygen saturation acquired by optical measurement.

9. The processing apparatus according to claim 8, wherein the optical measurement is performed by a pulse oximeter.

10. The processing apparatus according to claim 1, further comprising an ultrasound probe configured to transmit an ultrasound wave to the object and receive the ultrasound wave from the object.

11. The processing apparatus according to claim 10, wherein the processing unit is configured to perform the image reconstruction using a shape of the object acquired by transmission and reception of the ultrasound wave via the ultrasound probe.

12. The processing apparatus according to claim 10, wherein the processing unit is configured to detect the artery of the blood vessel by using a Doppler signal acquired using the ultrasound probe.

13. A processing apparatus comprising:
a processing unit configured to acquire image data indicating oxygen saturation distribution inside an object by using signals derived from acoustic waves which are generated by beams of light having a plurality of wavelengths irradiated to the object, wherein the processing unit is configured to:
acquire information on an oxygen saturation at a first position of a blood vessel of the object, generated by image reconstruction using the signals,
acquire a first correction amount to correct the information on the oxygen saturation at the first position of the blood vessel,
acquire a second correction amount to correct information on the oxygen saturation in a second position of the object other than the first position, based on the first correction amount,
acquire information on the oxygen saturations at a plurality of first positions in the blood vessel of the object, and
perform interpolation based on the second correction amount acquired for each of the plurality of first positions; and
a storage unit configured to store the information on an oxygen saturation at a first position, the information on the oxygen saturations at a plurality of first positions, the first correction amount, and the second correction amount so as to be readable by the processing unit.

14. A processing method for acquiring image data indicating information distribution on oxygen saturations inside the object by using signals derived from acoustic waves which are generated by beams of light having a plurality of wavelengths irradiated to an object, the method comprising:
acquiring an oxygen saturation at a first position of a blood vessel of the object, generated by image reconstruction using the signals;
acquiring a first correction amount to correct information on the oxygen saturation at the first position of the blood vessel;
acquiring a second correction amount to correct information on an oxygen saturation in a second position of the object other than the first position, based on the first correction amount; and
correcting information on the oxygen saturation in a peripheral area of the first position of the blood vessel by using the second correction amount.

15. A processing method for acquiring image data indicating information distribution on oxygen saturations inside the object by using signals derived from acoustic waves which are generated by beams of light having a plurality of wavelengths irradiated to an object, the method comprising:
acquiring an oxygen saturation at a first position of a blood vessel of the object, generated by image reconstruction using the signals;
acquiring a first correction amount to correct information on the oxygen saturation at the first position of the blood vessel;
acquiring a second correction amount to correct information on an oxygen saturation in a second position of the object other than the first position, based on the first correction amount, acquiring information on the oxygen saturations at a plurality of first positions in the blood vessel of the object; and performing interpolation based on the second correction amount acquired for each of the plurality of first positions.

\* \* \* \* \*